United States Patent [19]

Brusilovsky et al.

[11] 4,218,390

[45] Aug. 19, 1980

[54] METHOD FOR PREPARING BIURET-STRUCTURE POLYISOCYANATES

[76] Inventors: Mikhail G. Brusilovsky, Krymsky val, 8, kv. 56, Moscow; Valentin P. Krasnokutsky, Novouglicheskoe shosse, 65, kv. 51, Zagorsk; Galina I. Nemtinova, Leningradskee shosse, 48, kv. 151; Evgeny N. Novozhilov, Tulinskaya ulitsa, 18/2, kv. 1, both of Moscow; Viktor A. Pekarsky, ulitsa Kirova, kvartal 116, 24, kv. 30, Ljubertsy Moskovskoi oblasti; Svetlana A. Platonova, ulitsa Verkhnyaya, 22, Bykovo Moskovskoi oblasti; Alexandr S. Tumansky, Vyborskaya ulitsa, 10, kv. 71, Moscow, all of U.S.S.R.

[21] Appl. No.: 37,481

[22] Filed: May 9, 1979

[51] Int. Cl.$^2$ ............................................. C07C 127/24
[52] U.S. Cl. ............................................... 260/453 AB
[58] Field of Search .................................. 260/453 AB

[56] References Cited

U.S. PATENT DOCUMENTS

| 3,896,154 | 7/1975 | Takahashi et al. ............ 260/453 AB |
| 3,903,127 | 9/1975 | Wagner et al. ................ 260/453 AB |

*Primary Examiner*—Dolph H. Torrence
*Attorney, Agent, or Firm*—Haseltine, Lake & Waters

[57] ABSTRACT

A method for preparing biuret-structure polyisocyanates which comprises reacting 1,6-hexamethylenediisocyanate with water which is introduced into the reaction zone in the form of vapors in a mixture with air or an inert gas at a moisture content of said mixture of from 0.1 to 2.0 kg/kg and temperature of from 110° to 130° C. The reaction is carried out at a temperature ranging from 150° to 170° C.

The polyisocyanates having biuret structure as produced by the method according to the present invention have a molecular mass of about 800, the content of isocyanate groups is as high as 23.59%. No polyurea is formed in the reaction. The process is single-staged, technologically simple and can be performed continuously.

1 Claim, 1 Drawing Figure

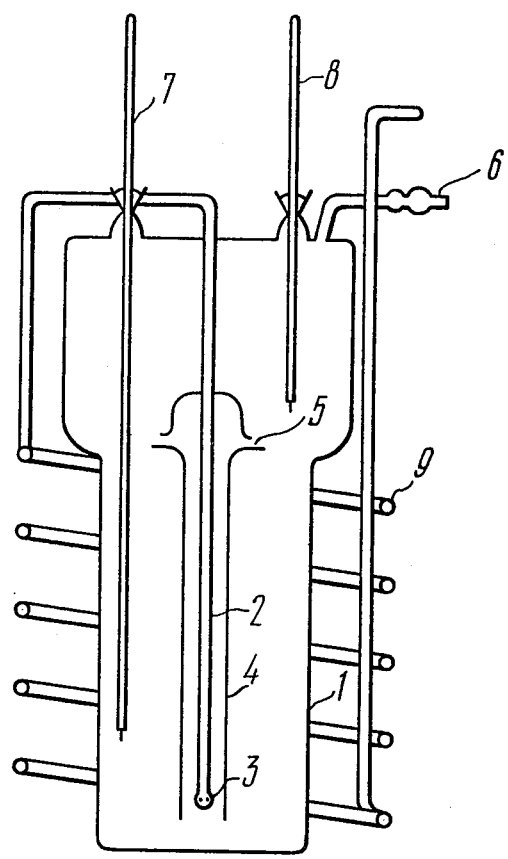

METHOD FOR PREPARING BIURET-STRUCTURE POLYISOCYANATES

FIELD OF THE INVENTION

The present invention relates to methods for preparing polyisocyanates having a biuret structure.

Said polyisocyanates are widely used in paint and varnish industry as an isocyanate component, e.g. they find an extensive use in polyurethane composition for the manufacture of light- and weather-resistant coatings.

BACKGROUND OF THE INVENTION

One of the main requirements imposed on biuret-structure polyisocyanates resides in the necessity of having optimum content of isocyanate groups which defines the product viscosity. The higher the content of isocyanate groups in the final product (greater amount of the reaction centres necessary for the formation of a protective coating), the lower the viscosity (which lowers the amount of a solvent in the preparation of paint and varnish compositions) and the higher is the product quality. The maximum theoretically possible content of isocyanate groups in the desired product is 26.36%. Practically it is smaller and varies from 21 to 24% depending on the process of manufacture.

Known in the art is a method for preparing biuret-structure polyisocyanates by way of reacting an aliphatic diisocyanate such as 1,6-hexamethylenediisocyanate with water (cf. FRG Patent No. 1,101,394). The process is conducted in two stages. In the first stage water is gradually charged into the starting diisocyanate and the mixture temperature is maintained at about 100° C. This stage is performed for a period of from 3 to 6 hours. As a result, a substituted urea is obtained. After the admission of the whole amount of water, the reaction mass temperature is elevated to 130°–140° C. or even up to 250° C. and stirring is continued for one additional hour to give a biuret-structure polyisocyanate. Then the resulting mass is filtered-off from the insoluble urea, the amount of which is 1 to 5%. The filtered-off product is subjected to vacuum distillation to remove the excessive 1,6-hexamethylenediisocyanate.

One of the disadvantages inherent in this prior art method resides in the formation of a by-product therein (insoluble urea) in an amount of from 1 to 5%. This has a detrimental effect on the desired product yield. Besides, the duration of the process of preparation of the polyisocyanate is rather long.

More effective is a single-stage method for producing a biuret-structure polyisocyanate (cf. USSR Inventor's Certificate No. 368282). In accordance with this process, gradual admission of water into the starting diisocyanate such as 1,6-hexamethylenediisocyanate, is effected at a temperature within the range of from 130° to 145° C., preferably from 135° to 138° C. In doing so, to minimize the amount of the forming by-product (polyurea in an amount of up to 0.01%), water is charged in the form of an aqueoacetone solution (I:I) at a rate of from 0.5 to 5 kg/hr per one m³ of the isocyanate volume. The reaction is proceeded to a content of isocyanate groups of from 32.5 to 34.5%. The resulting reaction mass is subjected to filtration on cartridge-type filters in order to remove the formed polyurea from the desired product and further subjected to vacuum distillation to remove the excessive 1,6-hexamethylenediisocyanate. The thus produced polyisocyanate having biuret structure has a molecular mass of from 700 to 850 (by the cryoscopic method) and a content of isocyanate groups is 21–23%.

This method also necessitates filtration to remove polyurea from the product. Therewith, despite the fact that the content of polyurea per se is small (0.01%), losses of isocyanates (1,6-hexamethylenediisocyanate and biuret-structure polyisocyanates) upon filtration are practically as high as 2% as calculated for the intermediate product. This is due to the fact that polyurea is liable to a strong swelling with isocyanates. Replacement of the spent filtering aid is also accompanied by losses of polyisocyanate.

This method also requires a long time for performing same. The synthesis of a biuret-structure polyisocyanate lasts for 4 to 24 hours. The process technology does not make it possible to provide a continuous method. Furthermore in the process use is made of hazardous acetone for dilution of water, through acetone per se is not a reactant in the process.

During the supply of a solution of water in acetone, the latter, while passing into 1,6-hexamethylenediisocyanate and the reaction products thereof heated to the temperature of 135° C., is evaporated and vented to atmosphere thus increasing, by 2 to 2.5%, the total losses of the starting materials.

BRIEF SUMMARY OF THE INVENTION

It is an object of the present invention to provide such a method for preparing biuret-structure polyisocyanates which would make it possible to obtain the desired product with reduced losses of 1,6-hexamethylenediisocyanate and simplify the process technology.

This and other objects of the present invention are accomplished by that in a method for preparing biuret-structure polyisocyanates according to the present invention by way of reacting 1,6-hexamethylenediisocyanate with water upon heating, in accordance with the present invention water is admitted into the reaction zone in the form of vapours in a mixture with air or an inert gas at a moisture content of the mixture of from 0.1 to 2.0 kg/kg and temperature of the mixture of 110° to 130° C., while the reaction is carried out at a temperature within the range of from 150° to 170° C.

Admission of water in the form of a vapour-gas mixture provides better conditions for dispersing of water in the reaction mass. This technological step makes it also possible to substantially lower the rate of formation of by-products, in particular insoluble polyurea, and to introduce greater amounts of water per unit time, thus reducing the process duration.

As the inert gas in accordance with the method of the present invention use can be made of any inert gas such as nitrogen, carbon dioxide.

The above-specified parameters are optimal. Thus, with decreasing moisture content of this vapour-gas mixture below the mentioned lower limit, probability of formation of the by-product is reduce, though the process rate is simultaneously decreased. Accordingly, with increasing the moisture content above 2.0 kg/kg, the process rate is increased, though the probability of formation of the by-product is also increased. As regards the vapour-gas mixture temperature, it should be equal to at least 110° C., otherwise condensation of water is possible and penetration thereof into the reaction zone in the form of droplets. The latter inevitably results in the formation of a by-product due to an increased local concentration of water in the reaction zone. On the other hand, increasing temperature of the vapour-gas mixture contributes to a greater saturation of the off-gases with vapours of 1,6-hexamethylenediisocyanate and, consequently, results in higher losses thereof with the off-gases. For this reason the optimum temperature of the vapour-gas mixture is varied within the range of from 110° to 130° C.

As it has been already mentioned hereinabove, the temperature of reaction between 1,6-hexamethylenediisocyanate and water is within the range of from 150° to 170° C. Temperature increase above 170° C. reduces the process duration, but results in the formation of high-molecular polyisocyanates having biuret structure, thus impairing properites of the final product. Lowering temperature below the specified lower limit increases probability of the by-product.

The biuret-structure polyisocyanate produced by the method according to the present invention has a molecular mass of about 800 and the content of isocyanate groups is about 23.59%. The resulting products contain no polyurea. The products have viscosity which is lower than the viscosity of biuret-structure polyisocyanates produced by the prior art methods.

Owing to the fact that no polyurea is formed in the process, losses of 1,6-hexamethylenediisocyanate are reduced and the process per se necessitates no labour-consuming filtration stage. This, in turn, makes it possible to perform the process continuously.

BRIEF DESCRIPTION OF THE DRAWING

The method for preparing a biuret-structure polyisocyanate according to the present invention is preferably performed in a reaction apparatus operating on the air-lift principle which is schematically shown in the accompanying drawing.

In accordance with the drawing, the reaction apparatus comprises a vessel 1 with a central tube 2 located thereinside and intended for the supply of a mixture of water vapours with air or an inert gas and provided with openings 3 at the end thereof. The central tube 2 is coaxially located inside the inner tube 4 thus forming an annular gap therebetween. The inner tube 4 is provided with overflow holes 5. The reaction apparatus is also provided with a tube 6 for discharging the off-gases. Inside said vessel 1 a thermometer 7 is placed for measurement of the reaction mass temperature and a thermometer 8 for measurement of the off-gas-temperature. Outside the vessel 1 a coil 9 is provided which communicates with the central tube 2.

DETAILED DESCRIPTION OF THE INVENTION

The method according to the present invention is performed in the above-described reaction apparatus in the following manner.

Into the vessel 1 mounted in an air-bath (not shown) 1,6-hexamethylenediisocyanate is charged and the contents being heated to a temperature of from 150° to 170° C. Through the coil 9 and the central tube 2 with openings 3 at its end a mixture of water vapours with air or an inert gas is admitted at a temperature of from 110° to 130° C. The mixture while being bubbled through the layer of 1,6-hexamethylenediisocyanate in said annular gap formed by the central tube 2 and inner tube 4 entrains 1,6-hexamethylenediisocyanate which is passed through the overflow holes 5 into the external zone of the apparatus and a fresh portion of 1,6-hexamethylenediisocyanate is sucked into the annular gap from the bottom part of the apparatus. In this manner agitation and circulation of the reaction mass is effected. The spent gas mixture along with carbon dioxide formed in the reaction is withdrawn from the apparatus via the pipe 6.

The resulting reaction mass comprises a solution of a biuret-structure polyisocyanate in the excessive amount of 1,6-hexamethylenediisocyanate. This mixture is charged into a rotary evaporator and the excess of 1,6-hexamethylenediisocyanate is distilled-off at a temperature ranging from 140° to 160° C. and under an absolute pressure of 2–5 mm Hg.

For a better understanding of the present invention, some specific Examples are given hereinbelow by way of illustration.

EXAMPLE 1

Into the vessel 1 of a reaction apparatus there are charged 250 g of 1,6-hexamethylenediisocyanate and the vessel contents is heated to the temperature of 150°–155° C. Through the coil 9 and central pipe 2 a mixture of water vapours and nitrogen is fed at the rate of 4 l/hr. This mixture has the moisture content of 2 kg/kg and temperature of 110° C. The mixture is bubbled through a layer of 1,6-hexamethylenediisocyanate. The spent gaseous mixture along with the formed carbon dioxide is withdrawn from the apparatus via the pipe 6. The synthesis duration is 126 minutes. As a result, a reaction mass is obtained which comprises a solution of polyisocyanate of the biuret structure in the excess of 1,6-hexamethylenediisocyanate. The reaction mass is charged into a rotary evaporator and the excessive amount of 1,6-hexamethylenediisocyanate is distilled-off at a temperature within the range of from 140° to 160° C. under the absolute pressure of 2 to 5 mm Hg. The resulting biuret-structure polyisocyanate has the following characteristics:
molecular mass—800
content of isocyanate groups—22.2%.
The desired product contains no polyurea.

EXAMPLE 2

Into the vessel 1 of the reaction apparatus there are charged 250 g of 1,6-hexamethylenediisocyanate and the vessel contents are heated to a temperature of from 160° to 166° C. A mixture of water vapours and air is fed through the coil 9 and the central tube 2 at the rate of 12 l/hr. This mixture has its moisture content of 0.75 kg/kg and temperature of 120° C. This mixture is bubbled through the layer of 1,6-hexamethylenediisocyanate. The spent gaseous mixture along with the formed carbon dioxide is withdrawn via the tube 6 from the apparatus. The synthesis duration is 60 minutes. As a result, a reaction mass is obtained comprising a solution of the biuret-structure polyisocyanate in the excessive amount of 1,6-hexamethylenediisocyanate. The reaction mass is charged into a rotary evaporator and the excess of 1,6-hexamethylenediisocyanate is distilled-off at a temperature of 140° to 160° C. under an absolute pressure of 2–5 mm Hg.

The resulting biuret-structure polyisocyanate has the following characteristics:
molecular mass—800
content of isocyanate groups—22.33%.
The desired product contains no polyurea.

EXAMPLE 3

Into the vessel 1 of the reaction apparatus there are charged 250 g of 1,6-hexamethylenediisocyanate and the vessel contents are heated to the temperature of 158°–162° C. A mixture of water vapours and nitrogen is fed through the coil 9 and the central pipe 2 at the rate of 12 1/hr. The moisture content of this mixture is 0.5 kg/kg and temperature is equal to 125° C. This mixture is bubbled through the layer of 1,6-hexamethylenediisocyanate. The spent gaseous mixture along with the formed carbon dioxide is withdrawn from the apparatus through the pipe 6. The synthesis duration is 66 minutes. As a result, a reaction mass is obtained which comprises a solution of the biuret-structure polyisocyanate in the excessive amount of 1,6-hexamethylenediisocyanate. The reaction mass is charged into a rotary evaporator and the excess of 1,6-hexamethylenediisocyanate is distilled-off at a temperature of from 140° to 160° C. under the absolute pressure of 2–5 mm Hg. The resulting biuret-structure polyisocyanate has the following characteristics:

molecular mass—750
content of isocyanate groups—23.59%.

The desired product contains no polyurea.

The products obtained in the foregoing Examples 1 to 3 comprise a transparent colourless or slightly yellow liquid.

The viscosities of the products obtained in Examples 1 to 3 are compared with those of standard samples of the biuret-structure polyisocyanate Desmodur N.

To this end, 70% solutions of the products in a mixture of xylene-ethylglycolacetate (weight ratio 1:1) are prepared; these solutions comprise the commercial form of the products. Viscosity (at the temperature of 25° C.) is determined using a capillary viscosimeter with the diameter of 0.6 mm; it is equal to: in the case of Desmodur N 657 sec., in the case of a sample produced from the product of Example 1—219 sec., for the sample of the product of Example 2—223 sec, for the sample prepared from the product of Examples 3—185 sec.

What is claimed is:

1. A method for preparing biuret-structure polyisocyanates comprising reacting 1,6-hexamethylenediisocyanate at a temperature ranging from 150° to 170° C. with water which is delivered into the reaction zone in the form of vapours in a mixture with a gas selected from the group consisting of air and an inert gas at a moisture content of said mixture ranging from 0.1 to 2.0 kg/kg and temperature of from 110° to 130° C.

* * * * *